(12) United States Patent
Popescu et al.

(10) Patent No.: US 7,039,163 B2
(45) Date of Patent: May 2, 2006

(54) METHOD FOR AUTOMATICALLY SETTING AN X-RAY DOSAGE FOR PRODUCING AN X-RAY TOMOGRAPHIC IMAGE

(75) Inventors: Stefan Popescu, Erlangen (DE); Christoph Süb, Erlangen (DE); Heiko Wolf, Erlangen (DE); Dietmar Hentschel, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

(21) Appl. No.: 10/660,395

(22) Filed: Sep. 11, 2003

(65) Prior Publication Data

US 2005/0058250 A1    Mar. 17, 2005

(51) Int. Cl.
*H05G 1/32* (2006.01)
*A61B 6/03* (2006.01)

(52) U.S. Cl. .................... 378/109; 378/207; 378/4
(58) Field of Classification Search ............. 378/4–20, 378/207, 109, 115, 116
See application file for complete search history.

(56) References Cited

U.S. PATENT DOCUMENTS

| 4,709,382 | A  | * | 11/1987 | Sones .................... 378/62 |
| 6,901,129 | B1 | * | 5/2005  | Tachizaki et al. ........ 378/4 |
| 2002/0075997 | A1 | * | 6/2002 | Unger et al. ............ 378/98.9 |

OTHER PUBLICATIONS

"Noise Due to Photon Counting Statistics in Computed X-Ray Tomography," Chesler et al, J. of Computer Assisted Tomography (Computed Tomography), vol. 1, No. 1 (1977) pp. 64–74.

* cited by examiner

*Primary Examiner*—Craig E. Church
*Assistant Examiner*—Krysytna Suchecki
(74) *Attorney, Agent, or Firm*—Schiff Hardin LLP (57) ABSTRACT

For automatically controlling or adjusting the X-ray dose when scanning an examination subject in a CT apparatus, a series of reference measurements are initially made by obtaining CT images of respective phantoms having different attenuation. The tube current for each phantom that produces an image of the phantom having an acceptable noise level, and thus an acceptable image quality, is stored in a table. In a subsequent CT scan of an examination subject, the tube voltage is automatically adjusted when irradiating a region of the subject having attenuation comparable to the attenuation of one of the phantoms, so as to employ the tube current when irradiating the examination subject that produced the image of acceptable quality for the comparable phantom.

3 Claims, 6 Drawing Sheets

METHOD FOR AUTOMATICALLY SETTING AN X-RAY DOSAGE FOR PRODUCING AN X-RAY TOMOGRAPHIC IMAGE

BACKGROUND OF THE INVENTION

1. Field of the Invention

The present invention is directed to a method for automatically setting an X-ray dosage for producing a tomographic image, using an X-ray CT device.

2. Description of the Prior Art

In the production of images of an examination subject in a computed tomography system, it is unavoidable that a certain level of noise will be present in the image. In general, the level of noise can be reduced by increasing the tube current, and thereby increasing the X-ray dose, however, obviously this cannot be done indiscriminately because overexposure of the examination subject to X-rays must be avoided.

Moreover, different portions of a human examination subject exhibit different attenuations, due to respectively different compositions and physical dimensions. Particularly in computed tomography examinations wherein a larger portion of the body is scanned, which may encompass such differently dimensioned body regions, it is undesirable, from the point of view of image quality, to select one and only one tube current/X-ray dose for the entire scan, because the dose may be suitable for scanning one portion of the subject, but may not be suitable for scanning another portion. If a single dose is employed for the entire scan, it must be selected at a compromise value.

Various investigations have been undertaken to analyze the relationship between the level of noise in a CT image, and the respective values of various parameters that are associated with the production of the CT image. One example of such an investigation is the article "Noise Due To Photon Counting Statistics In Computed X-Ray Tomography," Chesler et al., Journal of Computed Assisted Tomography, Volume 1, No. 1 (1977), pages 64–74.

SUMMARY OF THE INVENTION

It is an object of the present invention to provide a method for adjusting the X-ray dose in the production of a computed tomography image wherein an overall image with constant image quality is produced without overexposing the examination subject to X-rays.

The above object is achieved in accordance with the principles of the present invention in a method wherein the tube current is limited automatically at higher levels of attenuation of the examination subject, while still insuring appropriate image quality. A tube load computer, preferably mounted on the gantry of the CT apparatus, employs values obtained in reference measurements for different attenuation values and, dependent on the measured attenuation and the particular organ or body region being examined, the tube current is appropriately limited. The reference measurements can be obtained using a water phantom. On the basis of water phantoms having different attenuation, the interrelation of the desired image noise, tube current, maximum attenuation of the subject, and detector voltage are determined. These values are stored in a table for a particular tube voltage and slice thickness. The table is consulted by the load computer and operating parameters are set for examination of a particular organ or body region by selecting, from the table, the parameters for the water phantom having an attenuation most closely approximating the attenuation of the organ or region under examination.

DESCRIPTION OF THE PREFERRED EMBODIMENTS

First the theoretical interrelation between measurement system, absorption and noise is summarized and is applied to measurements on the Plus 4. Subsequently, procedures for automatic dosage are discussed.

The number of quanta N0 emitted by the tube during the measurement of a projection and of the slice fade-in h depends on the tube high voltage kV, the tube current IRöhre, the pre-filtering V and the wedge filter W:

$$N_0 = N_0(kV, I_{Röhre}, h, V, W) \tag{1}$$

Figure 1:
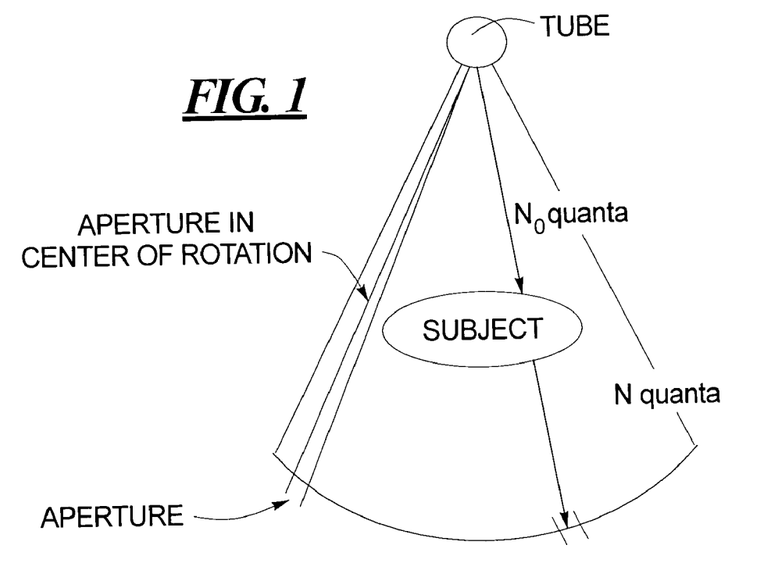
FIG. 1 is a schematic illustration of a CT apparatus for use in explaining the inventive method.

For a system as shown in FIG. 1, the pre-filtering can be assumed to be constant. The wedge filter causes a detector-channel-dependent variation of the quanta $N_0$. The high voltage, as well as the pre-filtering and wedge filter, determines the spectral energy distribution of the x-ray spectrum.

For the functional interrelation of N with the high voltage U, the tube voltage I, and slice thickness h, the following holds:

$$N = N_0 * \left(\frac{U}{U_0}\right)^{2.26} * \left(\frac{I}{I_0}\right) * \left(\frac{h}{h_0}\right) \tag{2}$$

It can be seen that $N \sim I$, $N \sim h$ and $N \sim U^{2.26}$. If U=const, h=const, then the number of quanta depends in a linear fashion on the tube current I.

After passing through a homogenous medium having thickness d and absorption µ, the following holds for the number of quanta N:

$$N = N_0 * e^{-\mu d} \tag{3}$$

The subject attenuation A is given as $$A = N_0/N \tag{4}$$

N is the number of quanta that impinge on the detector and produce the signal $U_{Det}$ in a channel of the detector:

$$U_{Det} = c * N \tag{5}$$

The constant c is a property of the detector that describes the absorption of the quanta and their conversion into an electrical signal (Signal/Quant). C depends on the spectral energy distribution of the x-ray spectrum and on the spectral sensitivity of the detector. Without an absorber, $N_0$ is to be used instead of N in equation (5).

The detector signal from equation (5) varies due to the quantum noise. In addition, the electronic noise $U_E$ must be taken into account. Thus, the following holds for the detector signal:

$$U_{Det} = U_{Quanten} + U_E \qquad (6)$$

The quantum noise is based on the Poisson statistic, so that the following holds:

$$U_{Quanten} = c*(\overline{N} \pm \sqrt{N}) = c*N \qquad (7)$$

In connection with equation (4), the following holds for the quantum noise $U_Q$ after passage through a subject having attenuation A:

$$U_Q = c * \sqrt{\frac{N_0}{A}} = \frac{U_0}{\sqrt{A*N_0}} \qquad (8)$$

According to equation (5), $U_0$ is the detector signal without absorber. From equation (8), it can be seen that there is an attenuation $A_0$ at which the quantum noise is equal to the electronic noise:

$$A_0 = (U_0/U_E)^2/N_0 = (c/U_E)^2 * N_0 \qquad (9)$$

Equation (6) can then be transformed to $$U_{Det} = c*N_0/A + c*\sqrt{N_0/A} + U_E \qquad (10)$$

Figure 2:
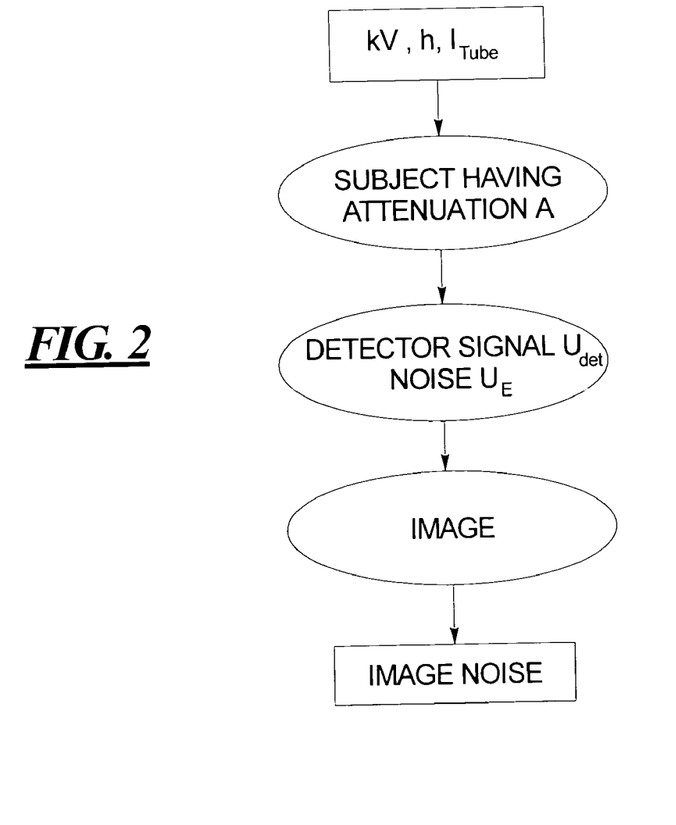
FIG. 2 is a flowchart illustrating the sources of noise in a CT image.

The detector signal thus depends on system-specific quantities (pre-filtering, wedge filter, detector constant c) that are equal for all modes of operation of the scanner, as well as on quantities (kV, $I_{Röhre}$, h) that are selected by the user, and of course also on the attenuation A of the subject of measurement. In addition to the noise of the measurement signal, which enters into the reconstruction via the line integral, the noise from the reconstruction itself must be taken into account as shown in FIG. 2.

For linear interpolation, the image noise σ of a homogenous water disk in the center of the measurement field is calculated as follows:

$$\sigma = \frac{500}{\mu_w \sqrt{a_D^3 NEQ}} q_r \qquad (11)$$

The relative noise factor $q_r$ takes into account the noise of the reconstruction algorithms. According to the definition, $q_r = 1$ for the Shepp-Logan core kernel with linear interpolation. $a_D$ is the scanning raster determined by the detector and related to the center of rotation. For the noise equivalent quanta, NEQ, the following holds:

$$NEQ = \frac{N_R * N_0}{a_D * A} \qquad (12)$$

$N_R$ is the number of readings per scan (number of projections*reading number, e.g. 1.5 sec: 1056 projections·2). From equations (11) and (12), the relation can be seen between the number of quanta (dosage), subject attenuation and image noise.

$$N_0 = \frac{A}{a_D^2 * N_R} * \left(\frac{500}{\mu_w * \sigma} * q_r\right)^2 \qquad (13)$$

The following table shows the results of a measurement of the 20 cm water phantom in the Plus4 (UFC detector) mode (Quality/Noise):

| Parameter | Value | Derived quantity |
|---|---|---|
| Mode | RED | Projections 1056   Reading number $N_R = 2$ |
| KV | 140 | $q_r = 1$ |
| mA | 146 | |
| TI | 1.5 | |
| SL | 10 | |
| Kernel | SP90 | |
| FOV | 250 0/0 | |
| Result | $\sigma_{140\,kV} = 8.76$ | |

With equation (13), $N_0$ can thus be calculated ($a_D = 0.34$ mm): $N_0 = 1.68 * 10^6$ For determining the electronic noise:

| | Measurement | | |
|---|---|---|---|
| Parameter | Value | | Evaluation |
| Mode | STATIC | | Analyze Load 00001.RCT |
| KV | 140 | | Row/Proj. Step:  2 |
| MA | 146 | | Format  μV |
| TI | 1.5 sec | | STAT/SD |
| SL | 10 mm | | WA (19) |
| SP90 | | | Column/Channel  lb = 350 |
| FOV | | | ub = 420 |
| Storage | FPA | | Row Stat -->MEAN |
| Control | X-ray | OFF | |
| platform | Anode Red | OFF | |
| Result | | | Average electronic noise $U_E$ in μV |

From the above values, $U_E = 32.93$ μV

For determining the strength of the detector signal:

| | Measurement | | |
|---|---|---|---|
| Parameter | Value | | Evaluation |
| Absorber | WITHOUT | | Analyze Load 00001.RCT |
| Mode | RED | | Row/Proj. Step:  2 |
| KV | 140 | | Format  μV |
| mA | 146 | | STAT/Mean |
| TI | 1.5 sec | | WA(18) |
| SL | 10 mm | | Column/Channel  lb = 350 |
| SP90 | | | ub = 420 |
| FOV | | | Row/STAT -->MEAN |
| Storage | FPA | | |
| Control | X-ray | ON | |
| platform | Anode Red | ON | |
| Result | | | Signal strength $U_0$ in μV |

From these values, $U_0 = 4460736$ μV

From equation (8), using the measurements it is thus possible to determine the quantum noise, and also the detector constant c, for each attenuation if a 12000-fold attenuation is assumed, $U_Q$=41 µV results.

Figure 3:
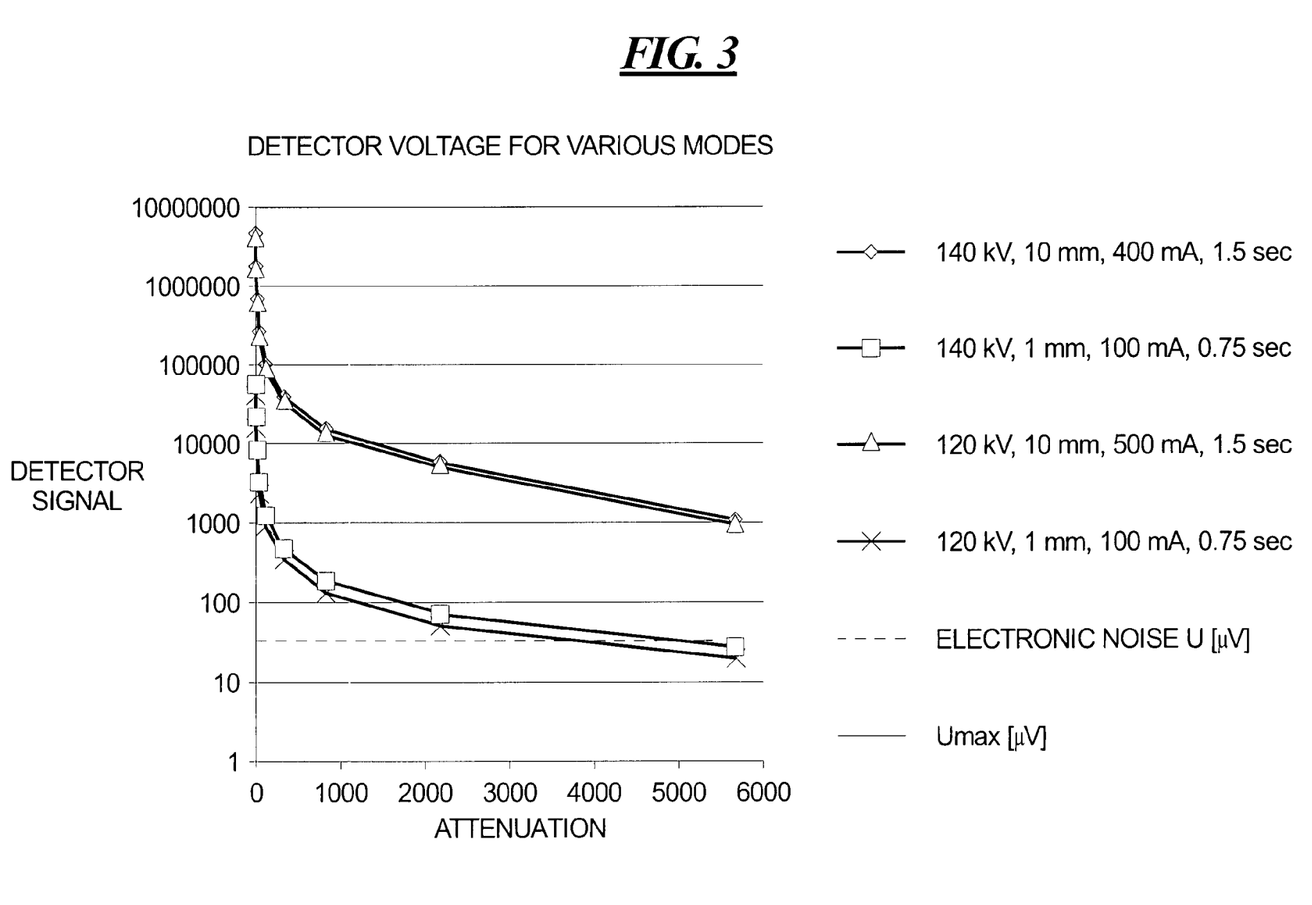
FIG. 3 is a graph showing the detector voltage for various modes of operation of a CT apparatus.

From equation (5), using the measured $U_0$ (sec. 4.3) and the value $N_0$ determined in sec. 4.1, the constant c can be determined as c=2.65 µV/Quant According to equation (10), $U_{Det}$=c*N/A holds for the detector signal without noise portions. N can be calculated according to equation (2). The rotation time TI can unproblemmatically be added to the equation. In 4.5, the constant c has been determined for the Plus 4 UFC detector. In FIG. 3, the strength of the detector signal is shown for various subject attenuations (water phantom) and measurement protocols. It is clear that for 1 mm slices, beginning with a subject attenuation of 4000 (corresponding to a water phantom 40 cm in diameter), the electronic noise is greater than the detector signal. The attenuation in the shoulder can reach a value of up to 10,000. FIG. 3 shows the detector voltage for various modes.

As can be seen from FIG. 2 noted earlier, the noise is composed of two portions: the noise from the measurement system (quanta and electronic noise) and the noise from the image reconstruction. The latter depends on subject properties (A, $\mu_w$), system parameters ($a_D$), recording parameters ($N_R$, $N_0$) and parameters of the image reconstruction (interpolation, kernel [$q_r$]). Subject properties and system parameters cannot be influenced; the parameters of the image reconstruction are normally fixed by the organ mode used, so that $N_0$, i.e. the tube current, remains as a variable quantity that has to be optimized online during the measurement. The matching of the tube current to the maximum subject attenuation during rotation is necessary.

The determination of the subject attenuation is already part of the dosage modulation and can be taken over. For a single line (or row) detector, this involves:
1. Offset correction of the raw data
2. Smoothing of the projections (e.g. sliding [or: variable, flexible] averaging)
3. Norming of the data ($U_{Monitor}/U_k$), $U_k$=Signal of the k-th detector channel
4. Calculation of the maximum of all detector channels.

The optimal dosage is determined by means of reference measurements. Since Equation (11) was calculated for round, homogenous water phantoms, at first only such phantoms need be considered. On the basis of water phantoms having different attenuation, the interrelation of the desired image noise σ, tube current $I_{Ref}$, maximum attenuation A of the subject and detector voltage $U_{Det}$ are determined. These values, $U_{Det}$(A, σ, I), are stored in a table for a particular tube voltage $U_{kV}$ and slice thickness h.

If σ is fixedly predetermined, i.e., the kernel is not modified, then it is sufficient to consider the detector signal $U_{Det}$. From equations (6) and (7), the following results:

$$U_{Det} = c * \frac{N_0}{A} + U_E \qquad (14)$$

For an acceptable image quality, the electronic noise must be negligible. Dependent on the attenuation A, a minimum tube current I is to be predetermined, so that $c*N_0/A > U_E$ holds. $U_{det}$ is then simplified to $$U_{Det} = c * \frac{N_0}{A} \qquad (15)$$

$U_{Det}^{Ref,\sigma}$, $N_o^{Ref}$, $A^{Ref}$ are the parameters for the reference measurement of a phantom having attenuation A, so that for a given dosage $N_0$ an image noise a and a detector signal $U_{Det}$ is produced. If a subject having a different attenuation $A^{act}$, i.e., a different diameter, is now measured, then $N_0^{act}$ is to be adapted so that the following holds:

$$U_{Det}^{Ref,\sigma} = U_{Det}^{act} \qquad (15)$$

Applying equations (2) and (15), the following results:

$$\frac{A_{act}}{A_{Ref}} = \left(\frac{U_{act}^{kV}}{U_{Ref}^{kV}}\right)^{2.26} * \left(\frac{I_{act}}{I_{Ref}}\right) * \left(\frac{h_{act}}{h_{Ref}}\right) \qquad (16)$$

In addition, equation (16) takes into account the tube voltage and the slice thickness. If these are not modified, the new tube current $I_{act}$ can be calculated:

$$I_{act} = \frac{A_{act}}{A_{Ref}} * I_{Ref} \qquad (17)$$

Figure 4:
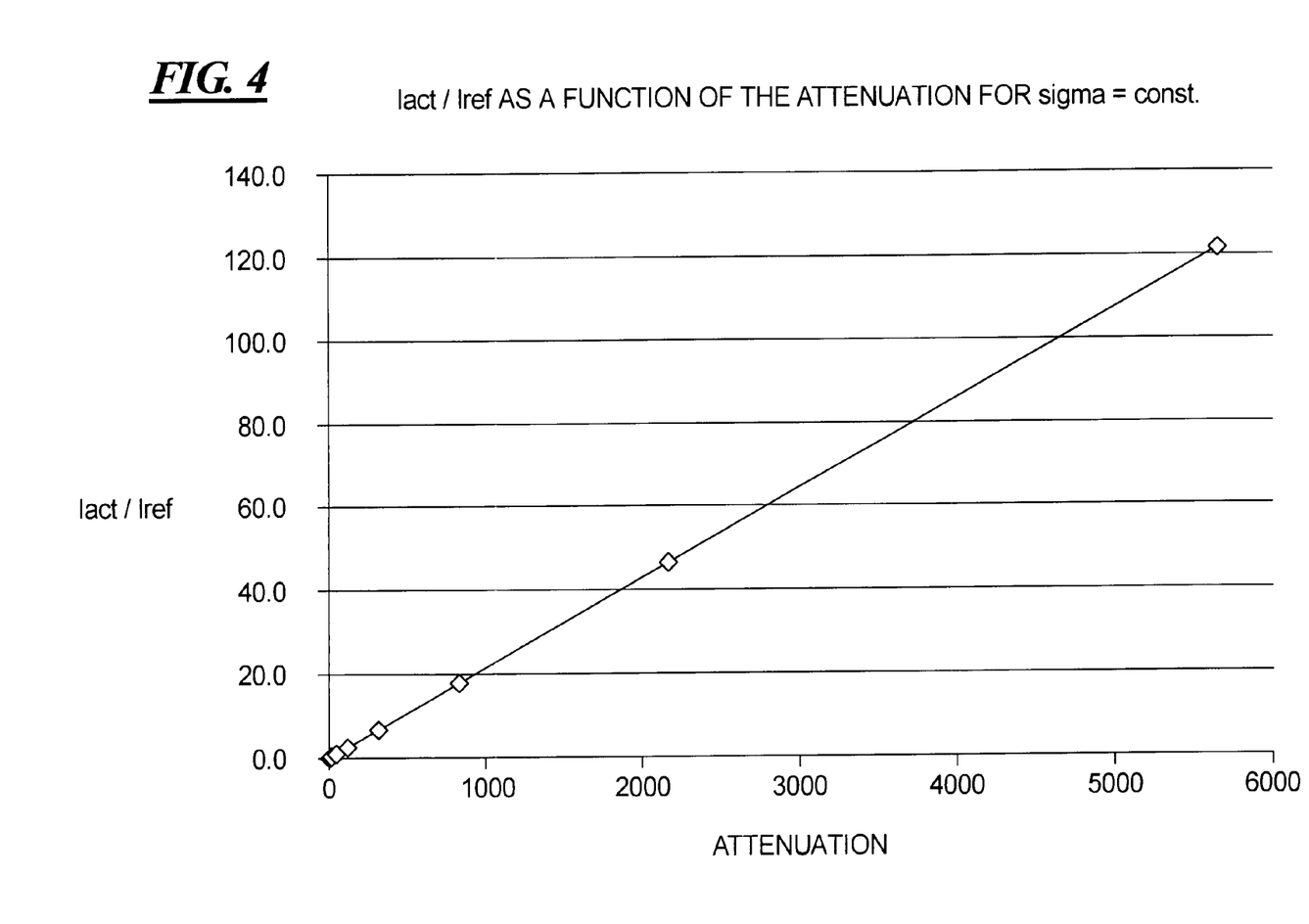
FIG. 4 is a graph showing the ratio of the actual tube current to a reference tube current as a function of attenuation.
Figure 5:
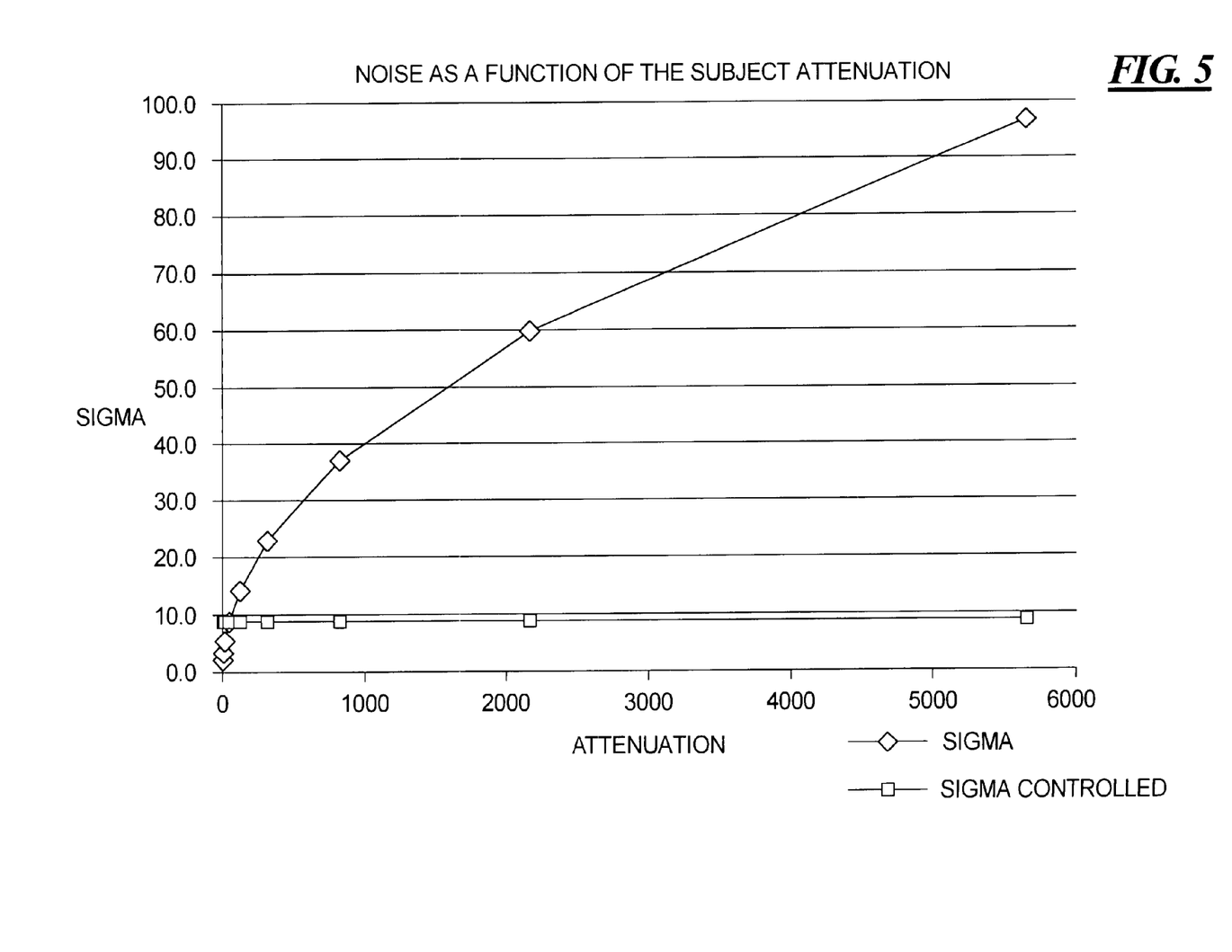
FIG. 5 is a graph showing noise as a function of the subject attenuation.

FIG. 4 a was calculated corresponding to equation (17), whereby a round water phantom having a diameter of 20 cm (A=46.5) was used as a reference, and norming took place to $I_{ref}$=146 mA (see sec. 4). It is clear that for phantoms having a diameter of greater than 25 cm, corresponding to an attenuation of 122, the required tube current can no longer be set! In the shoulder region, the attenuation is greater than 10000! It is therefore necessary to permit a higher degree of noise as the attenuation increases. In FIG. 5, the noise is plotted over the attenuation, if the tube current is held constant (blue curve) and the tube current according to FIG. 4 is increased.

Because the maximum tube current $I_{max}$ is predetermined by the system, it is necessary to ensure that $I_{act} < I_{max}$ continues to hold. However, in clinical application the outlook is not as negative as it appears according to FIGS. 4 and 5. It will not be expected to examine a shoulder with the low degree of noise of an abdominal measurement.

Figure 6:
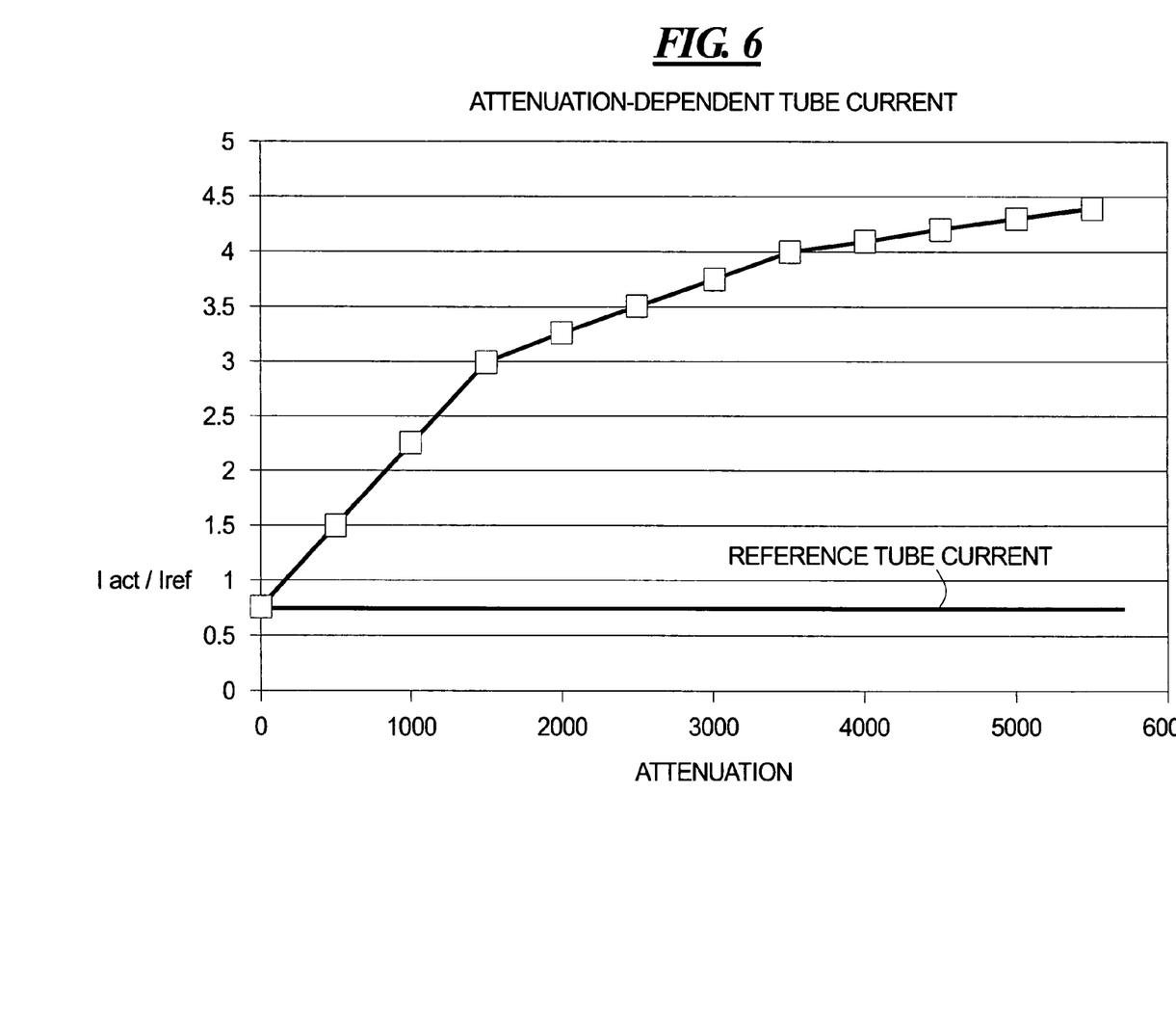
FIG. 6 shows the attenuation-dependent tube current for use in the inventive method.

The tube current can be limited by reducing the gradient of the change of the momentary tube current with increasing attenuation. In FIG. 6, this is achieved by dividing the attenuation region into three segments having decreasing gradients. Comparison with FIG. 4 shows that the increase in the tube current is reduced from a factor of 120 to a factor of 5. The division of the attenuation can ensue in a further region having respectively different gradients, so that there results from equation (17):

$$I_{act} = g(\text{organ}, A_{organ}) \frac{A_{act}}{A_{Ref}} * f_{user} * I_{Ref} \qquad (18)$$

g (organ, $A_{organ}$) is predetermined dependent on the organ mode and the maximum attenuation, if this is known for example from topogram measurements.

$F_{user}$ is a factor permitting the user to adjust the reference current $I_{Ref}$ to his preference in order to achieve a lower degree of noise or a higher savings in dosage. The factor should be adjusted once and then left unchanged.

As in dosage modulation, in automatic dosage the tube current is also modified online during the measurement. In contrast to modulation, which in the present implementation only reduces the tube current, in automatic dosage it is necessary to increase the current.

Figure 7:
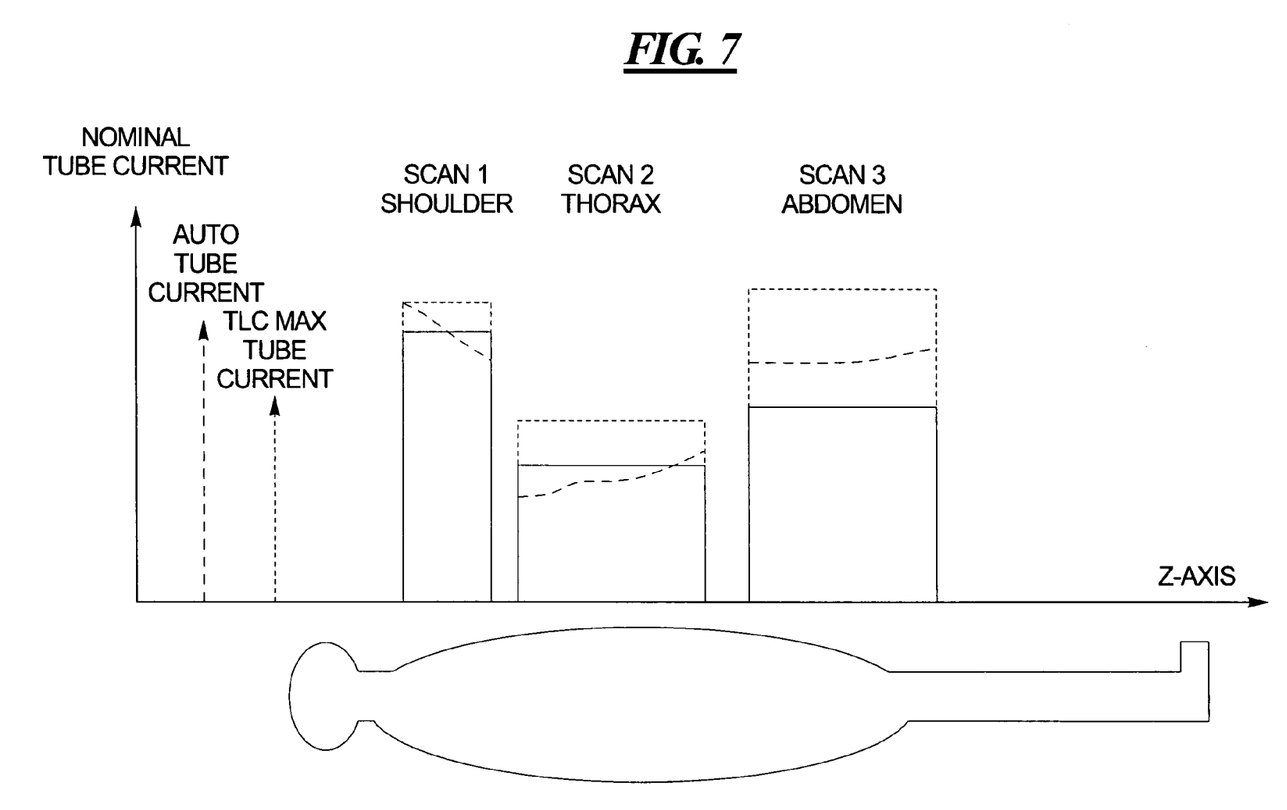
FIG. 7 schematically illustrates adjustment of the tube current in accordance with the invention for scanning different body regions.

One approach is shown in FIG. 7, wherein the automatic control in accordance with the invention is designated "auto." As was also previously the case, the tube load computer takes into account the nominal currents required by the user for the selected organ program, and interactively carries out an optimization process in order to avoid cooling pauses. If the maximum thermal tube load is not achieved using the prescribed scanning protocol, the load computer simulates possible maximum limits. In this way, the nominal currents of all scans can be increased proportionally, or the magnitude of the increase of the currents takes place in an organ-specific manner. These limits are downloaded for control purposes, and predetermine the maximum range of variation for the tube current.

The following table describes the scans shown in FIG. 7:

TABLE 1

| Currents | Remark | Scan 1 | Scan 2 | Scan 3 |
|---|---|---|---|---|
| $I_{nom}$ | Selected by user | $I_{nom}^1$ | $I_{nom}^2$ | $I_{nom}^3$ |
| $I_{TLC\ max}$ | Calculated by TLC | $I_{TLC\ max}^1$ | $I_{TLC\ max}^2$ | $I_{TLC\ max}^3$ |
| $I_{auto}$ | Tube current of the automatic dosage | $I_{auto}^1$ (Rotation) | $I_{auto}^2$ (Rotation) | $I_{auto}^3$ (Rotation) |

$$I_{auto}^i(\text{Rotation}) <= I_{TLC\ max}^i \quad i=\text{scan number} \qquad (18)$$

An online tube load computer can be located on the gantry, which monitors the tube load during the measurement and limits the momentary tube current, so that all planned scans can be measured with a "reasonable" tube current. It is to be avoided that, for example, two of three spirals are measured with an optimal tube current, while the current must be very strongly reduced for the third.

In examinations using contrast agents, a scan region is measured twice. The control unit notes the maximum attenuation and the modulation function and applies them in the second scan. If necessary, interpolation can take place in the z direction.

The maximum attenuation is determined ahead of time from two orthogonal topograms. Using the algorithm that is also used in the control unit for the interrelation between attenuation and tube current, a good estimation of the required tube current can be produced ahead of time.

Although modifications and changes may be suggested by those skilled in the art, it is the intention of the inventors to embody within the patent warranted hereon all changes and modifications as reasonably and properly come within the scope of their contribution to the art.

We claim:

1. A method for automatically controlling X-ray dosage for producing an image by computed tomography, comprising the steps of:

using an X-ray tube in a computed tomography apparatus operable with a tube current, obtaining a plurality of reference measurements by irradiating a plurality of different phantoms, with respectively different radiation attenuation, with X-rays from the X-ray tube, to produce a computed tomography image of each phantom;

for each image of each of said phantoms, setting a tube current of said X-ray tube that produces a predetermined level of noise in the image for that phantom representative of an acceptable image quality; and subsequently obtaining attenuation data from an examination subject for producing a computed tomography image of the examination subject with said computed tomography apparatus by irradiating the examination subject with X-rays from said X-ray tube, and automatically limiting the tube current of the X-ray tube, online while obtaining said attenuation data, for respective regions of said examination subject exhibiting attenuation comparable to the attenuation of at least one of said phantoms, dependent on the reference measurement for said at least one of said phantoms, to obtain a noise level and image quality in the image of said at least one region of the examination subject comparable to the noise level and image quality in the image of said at least one of said phantoms.

2. A method as claimed in claim 1 comprising employing a water phantom as said phantom.

3. A method as claimed in claim 2 comprising storing values for each reference measurement for each phantom in a table for different load currents, and automatically adjusting said tube current with a tube load computer, connected to said X-ray tube and having access to said table, while irradiating said examination subject.

* * * * *